US008143195B2

(12) United States Patent
Wang et al.

(10) Patent No.: US 8,143,195 B2
(45) Date of Patent: Mar. 27, 2012

(54) ARRAYS FOR BRINGING TWO OR MORE REAGENTS IN CONTACT WITH ONE OR MORE BIOLOGICAL TARGETS AND METHODS FOR MAKING AND USING THE ARRAYS

(76) Inventors: Yingjian Wang, New Britain, CT (US); Yingyi Wang, New Britain, CT (US)

( * ) Notice: Subject to any disclaimer, the term of this patent is extended or adjusted under 35 U.S.C. 154(b) by 2008 days.

(21) Appl. No.: 09/767,538

(22) Filed: Jan. 23, 2001

(65) Prior Publication Data
US 2003/0099927 A1    May 29, 2003

(51) Int. Cl.
*C40B 40/00* (2006.01)
(52) U.S. Cl. .......................................................... 506/13
(58) Field of Classification Search ................. 435/5–6, 435/721, 174, 455, 320.1, 440, 7.1, 287.2; 422/57; 436/518, 524, 529, 531, 805, 807
See application file for complete search history.

(56) References Cited

U.S. PATENT DOCUMENTS

| | | | |
|---|---|---|---|
| 4,750,100 A | 6/1988 | Ragsdale | |
| 4,910,140 A | 3/1990 | Dower | |
| 5,143,854 A | 9/1992 | Pirrung | |
| 5,149,655 A | 9/1992 | McCabe et al. | |
| 5,283,173 A | 2/1994 | Fields et al. | |
| 5,429,807 A | 7/1995 | Matson et al. | |
| 5,516,635 A | 5/1996 | Ekins et al. | |
| 5,616,745 A | 4/1997 | Behr et al. | |
| 5,702,896 A | 12/1997 | Collins et al. | |
| 5,744,305 A | 4/1998 | Fodor et al. | |
| 5,807,522 A | 9/1998 | Brown et al. | |
| 5,811,274 A * | 9/1998 | Palsson | 435/456 |
| 5,851,818 A | 12/1998 | Huang et al. | |
| 5,854,224 A * | 12/1998 | Lockett et al. | 514/44 |
| 6,083,763 A * | 7/2000 | Balch | 436/518 |
| 6,180,348 B1 | 1/2001 | Li | |
| 6,197,506 B1 | 3/2001 | Fodor et al. | |
| 6,197,599 B1 * | 3/2001 | Chin et al. | 436/518 |
| 6,274,321 B1 * | 8/2001 | Blumberg | 435/6 |
| 6,365,349 B1 * | 4/2002 | Moynihan et al. | 435/6 |
| 6,544,790 B1 * | 4/2003 | Sabatini | 435/455 |

FOREIGN PATENT DOCUMENTS
WO    95/35505    * 12/1995

OTHER PUBLICATIONS

U.S. Appl. No. 60/154,737, filed Sep. 17, 1999 to Sabatini.*
Reek et al., BioTechniques 19:282, 1995.*
Chen et al., "High-Efficiency Transformation of Mammalian Cells by Plasmid DNA", *Molecular and Cellular Biology*, Aug. 1987, pp. 2745-2752.
Derise et al., "Use of a cDNA Microarray to Analyse Gene Expression Patterns in Human Cancer", *Nature Genetics*, Dec. 1996, vol. 14, pp. 457-460.
Dick et al., "Gene Transfer into Normal Human Hematopoietic Cells Using In Vitro and In Vivo Assays", *Blood*, Aug. 1, 1991, vol. 78, No. 3, pp. 624-634.
Felgner et al., "Lipofection: A Highly Efficient, Lipid-Mediated DNA-Transfection Procedure", *Proc. Natl. Acad. Sci USA*, Nov. 1987, vol. 84, pp. 7413-7417.
Firth et al., "Improved Procedure for Electroporation of Peptides into Adherent Cells in Situ", *BioTechniques*, 1997, vol. 23, No. 4, pp. 644-646.
Fodor et al., "Light-Directed, Spatially Addressable Parallel Chemical Synthesis", *Science*, Feb. 15, 1991, vol. 251, pp. 767-773.
Gao et al., "Potentiation of Caitonic Liposome-Mediated Gene Delivery by Polycations", *Biochemistry*, 1996, vol. 35, No. 3, pp. 1027-1036.
"A Simple Procedure to Increase Efficiency of DEAE-Dextran Transfection of COS Cells", *TIG*, Jun. 1995, vol. 11, No. 6, pp. 216-217.
Graham et al, "A New Technique for the Assay of Infectivity of Human Adenovirus 5 DNA", *Virology*, 1973, vol. 52, pp. 456-467.
Guesdon et al., "Magnetically Responsive Polyacrylamide Agarose Beads for the Preparation of Immunoabsorbents", *Journal of Immunological Methods*, 1978, vol. 21, pp. 59-63.
Hacia, J.G., "Resequencying and Mutational Analysis Using Oligonucleotide Microarrays", *Nature Genetics Supplement*, Jan. 1999, vol. 21, pp. 42-47.
Hofland et al., "Formation of Stable Cationic Lipid/DNA Complexes for Gene Transfer"; *Proc. Natl. Acad. Sci. USA*, Jul. 1996, vol. 93, pp. 7305-7309.
Kononen et al., "Tissue Microarrays for High-Throughput Molecular Profiling of Tumor Specimens"; *Nature Medicine*, Jul. 1998, vol. 4, No. 7, pp. 844-847.
Lehrach et al., "Hybridization Fingerprinting in Genome Mapping and Sequencing", *Genetic and Physical Mapping; Genome Analysis vol. 1: Genetic and Physical Mapping*, Cold Spring Harbor Laboratory Press, K.E. Davies & S.M. Tilghman, editors, 1990, pp. 39-81.
Liu et al., "Cationic Liposome-Mediated Intravenous Gene Delivery"; *The Journal of Biological Chemistry*, Oct. 20, 1995, vol. 270, No. 42, pp. 24864-24870.

(Continued)

*Primary Examiner* — Jeffrey S. Lundgren
(74) *Attorney, Agent, or Firm* — Mirick, O'Connell, DeMallie & Lougee, LLP

(57) ABSTRACT

An array for bringing two or more reagents in contact with one or more biological targets comprising, two or more reagents; and one or more barriers adapted to at least temporarily maintain said reagents in at least one arrangement of two or more reagent portions so that said portions do not commingle with each other, wherein each said portion is maintained at a predefined locale in said arrangement so that each of said portions is adapted to be brought into contact with one or more biological targets; and methods for making and using same.

51 Claims, 3 Drawing Sheets

OTHER PUBLICATIONS

Schena et al.,, "Quantitative Monitoring of Gene Expression Patterns with a Complementary DNA Microarray"; *Science*, Oct. 20, 1995, vol. 270, pp. 467-470.

Shigekawa et al., "Electroporation of Eukaryotes and Prokaryotes: A General Approach to the Introduction of Macromolecules into Cells"; *BioTechniques*, 1988, vol. 6, No. 8, pp. 742-751.

Ternynck et al., "Polyacrylamide-Protein Immunoadsorbents Prepared with Glutaraldehyde"; *Febs Letters*, Jun. 1972, vol. 23, No. 1, pp. 24-28.

Wigler et al., "DNA-Mediated Transfer of the Adenine Phosphoribosyltransferase Locus into Mammalian Cells"; *Proc. Natl. Acad. Sci. USA*, Mar. 1979, vol. 76, No. 3, 1373-1376.

Williams et al., "Introduction of Foreign Genes into Tissues of Living Mice by DNA-coated Microprojectiles"; *Proc. Natl. Acad. Sci. USA*, Apr. 1991, vol. 88, pp. 2726-2730.

Yang et al., "Efficient In Situ Electroporation of Mammalian Cells Grown on Microporous Membranes"; *Nucleic Acids Research*, 1995, vol. 23, No. 15, pp. 2803-2810.

Bordignon et al., "Gene Therapy in Peripheral Blood Lymphocytes and Bone Marrow for ADA Immunodeficient Patients"; *Science*, Oct. 20, 1995, vol. 270, pp. 470-475.

Bulyk et al., "Quantifying DNA-Protein Interactions by Double-Stranded DNA Arrays", *Nature Biotechnology*, Jun. 1999, vol. 17, pp. 573-577.

* cited by examiner

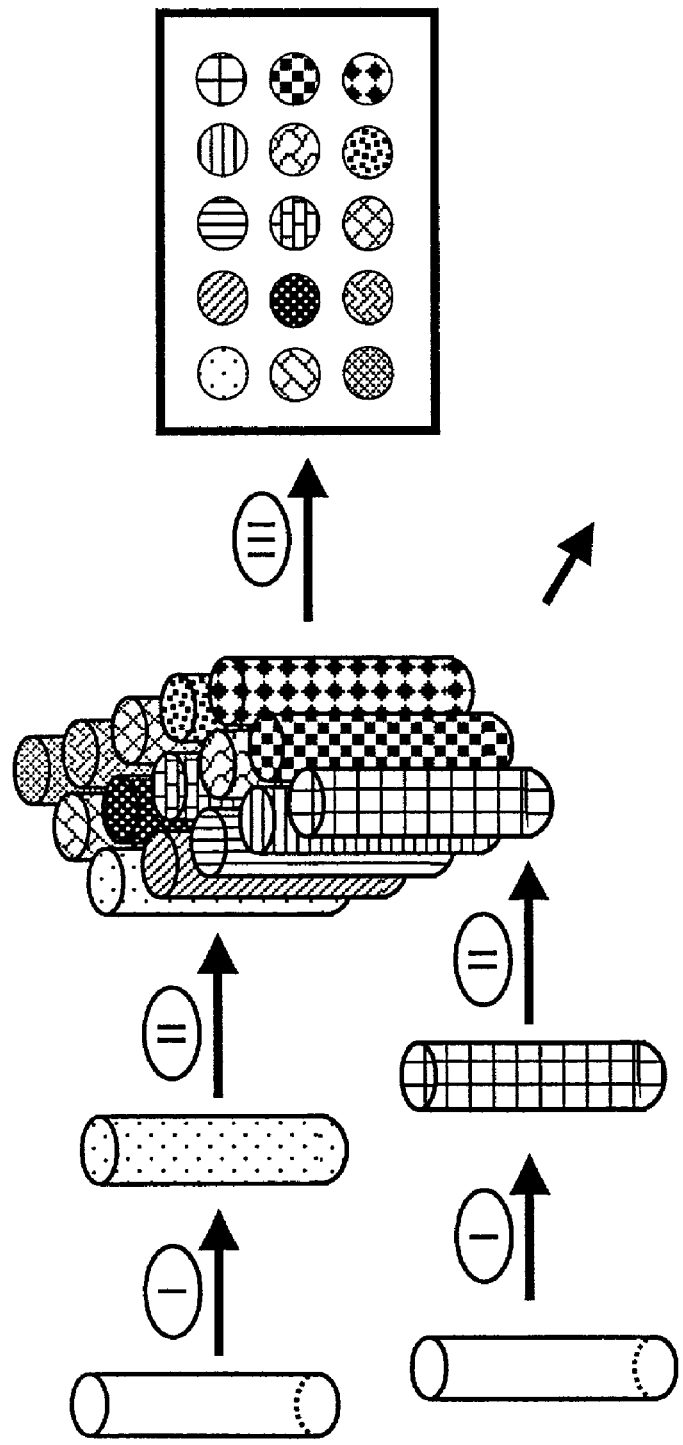

FIG. 1 illustrates, in a partially schematic view, showing a bundle of capillary tubes, each of which can be filled with a specific biological reagent and its position is pre-defined.

Figure 1: Schematic view of one embodiment of the production of transfection arrays.
I: Fill a plurality of capillary tubes with with biological reagents; each in an individual tube.
II: Bundle the capillary tubes together, with each tube with a specific biological reagent at a pre-determined position.
III: The arrays of capillary tubes can be further cut across sections to produce arrays with any desired height.

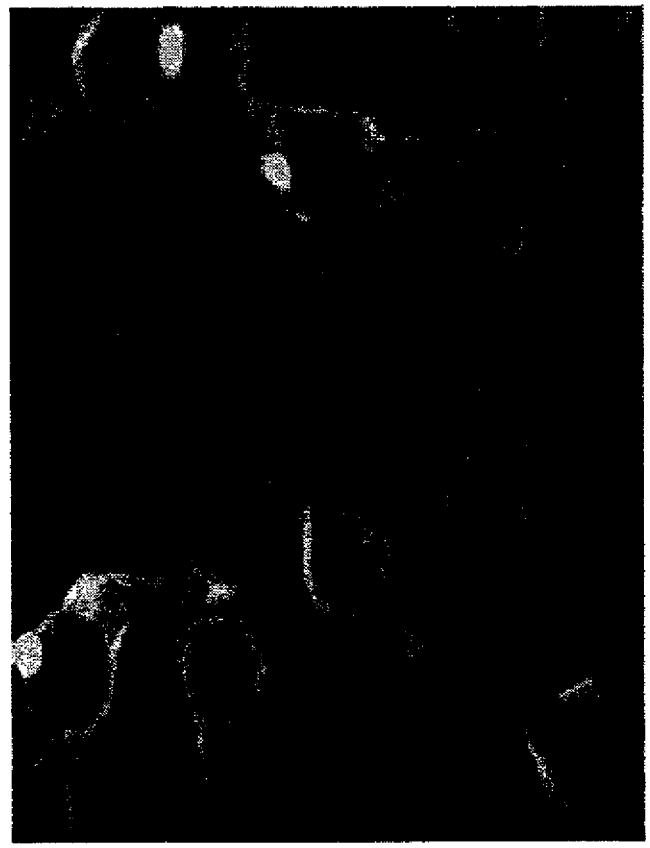
FIG. 2 is an example in which an array of 100 DNA were transfected into adherent COS7 cells by electroporation.

FIG. 3 is an example in which 10 different antibodies were used to stain mouse L cells

ARRAYS FOR BRINGING TWO OR MORE REAGENTS IN CONTACT WITH ONE OR MORE BIOLOGICAL TARGETS AND METHODS FOR MAKING AND USING THE ARRAYS

FIELD OF THE INVENTION

The present invention relates to novel arrays of biological reagents and methods for making and using the arrays.

BACKGROUND OF THE INVENTION

The availableness of a large number of biological reagents, such as hundreds of thousands of deoxyribonucleic acids (DNA) clones, numerous antibodies and recombinant proteins, millions of compounds obtained through combinatory chemical synthesis, has promoted the development of technologies for high throughput studies of these molecules. Special arrays of biological reagents have been designed, in which each of the reagents is placed at a pre-defined position and can be identified later by the position. These arrays of biological reagents have found a wide variety of applications. Protein arrays have been applied in studying protein expression patterns, protein posttranslational modifications such as phosphorylation, glycosylation, lipidation and ubiquitination. Protein arrays are also used in screening protein-protein interactions (Wang et. al., Mol. Cell Biol. 20, 4505-12). Arrays of nucleic acids are used for large scale hybridization assays, including monitoring of gene expression (Schena et al., 1995, Science 270:467-470; DeRisi et al., 1996, Nature Genetics 14:457-460), genetic and physical mapping of genomes, genetic diagnosis, genotyping of organisms, detection of DNA-protein interactions (Bulyk et al. Nature Biotechnology, 17:573-577, 1999), and distribution of biological reagents to researchers (see U.S. Pat. No. 5,807,522). DNA arrays are also used to obtain nucleotide sequence information, including mutation detection, polymorphism detection and DNA sequencing (Hacia, Nature Genetics Volume 21, supplement, p42-47, 1999). In addition, arrays of cells, tissues, lipids, polymers, drugs or chemical substances can be fabricated for large scale screening assays in medical diagnostics, drug discovery, molecular biology, immunology and toxicology (see Kononen J, et al., Nature Medicine, 4:844-7, 1998).

A variety of methods are currently available for making arrays of biological reagents, such as arrays of nucleic acids and proteins. One method for making an ordered array of DNA on a porous membrane is a "dot blot" approach, in which a plurality of DNA in solutions are transferred by vacuum to a porous membrane. A common variant of this procedure is a "slot blot" method in which the wells have highly elongated oval shapes. A more efficient way for making ordered arrays of molecules uses an array of pins dipped into the wells, e.g., the 96 wells of a microtitre plate, for transferring an array of samples to a substrate, such as a porous membrane. The pins can be designed to spot a membrane in a staggered fashion, for creating an array of thousands of spots in a small area (see Lehrach, et al., Hybridization fingerprinting in genome mapping and sequencing, genome analysis, Vol 1, Davies and Tilgham, Eds, Cold Spring Harbor Press, pp. 39-81, 1990). Recently Brown et al. (U.S. Pat. No. 5,807,522) described a more elaborated method to make arrays. The method involves dispensing a known volume of a reagent at each selected array position, by tapping a capillary dispenser on the support under conditions effective to draw a defined volume of liquid onto the support.

An alternate method of creating ordered arrays of nucleic acid sequences was described by Fodor, et al. (Science, 251: 767-773, 1991). The method involves synthesizing different nucleic acid sequences at different discrete regions of a support, usually made of glass. A related method was described by Matson, et al. (U.S. Pat. No. 5,429,807, 1995). A method of making arrays of polypeptides by photolithographic solid phase synthesis was described by Pirrung, et al. (U.S. Pat. No. 5,143,854, 1992).

Since in prior arts, arrays of biological reagents are mainly used in binding assays, such as DNA-DNA hybridization, DNA-RNA hybridization, DNA-protein binding, RNA-protein binding and protein-protein binding, DNA and protein arrays are accordingly fabricated for the purpose of performing these assays. For example, in dot blot or slot blot method, DNA are usually immobilized by baking or by exposing to UV radiation; and in DNA Chip manufactured by Affymatrix, oligo nucleotides are synthesized on glass supports through covalent bonds. Strong immobilization through covalent or multi-valent non-covalent bonds is necessary for binding or hybridization assays, which require extended incubations and multiple washes. However, covalent or very strong non-covalent immobilization used in making DNA or protein arrays by previous methods is not suitable for some other potential applications. For example, it is difficult to introduce DNA covalently bond to a support into cells. Therefore, the support materials and immobilization methods in prior arts are not suitable for introducing a large number of DNA or proteins into cells. The applications of DNA and protein arrays are thus severely limited. New techniques are needed to make arrays that can be used not only for binding assays but also for other applications, such as transfecting cells with arrays of DNA or proteins; and staining cells with arrays of antibodies.

Transfection is in general term the method to introduce biological reagents into target cells. The biological reagents, such as proteins, DNA and ribonucleic acids (RNA), are normally unable to cross cell membranes and enter cells. Transfection usually includes the steps of contacting the target cells with the reagents to be transfected, applying a condition such as an electric field to make cells uptake the reagents. There are many methods for transfection and they are referred by different names in prior arts. Transformation sometimes refers to the process of introducing a piece of DNA, usually in a vector, into bacteria. Infection is the process to deliver nucleic acids into cells by viruses. Numerous cell types have been transfected, which include bacteria, yeast, plant cells, insect cells, mammalian cells and human cells. Cells from a given source, e.g., a tissue, or an organ, or cells in a given state of differentiation, or cells associated with a given pathology or genetic makeup can be transfected.

Transfection of biological reagents into cells has a variety of applications. One of them is to study the functions of DNA and proteins. For examples, if introduction of an antibody against a protein into cells causes the cells to behave abnormally, then the function of the protein can be inferred from this abnormal phenotype. Likewise, after introducing an exogenous gene into a cell line, one can study the effects of the gene on cell growth, cell death and other cell behaviors. The regulation of the transfected gene, either its expression or activity, can also be studied.

Another application of transfection is to isolate genes of interest. A standard protocol for this application involves transfecting cells with a pool of DNA; selecting the transfected cells with a desired phenotype and recovering the DNA from the cells. Such techniques include but are not limited to expression cloning, complementary DNA (cDNA) libraries screening, expression library screening (see Sambrook et al., Molecular Cloning, a laboratory manual, Cold Spring Harbor Press, 1989) and yeast two-hybrid screening (see U.S. Pat. No. 5,283,173). Many genes encoding ion channels, membrane receptors and signaling proteins have been isolated using these techniques.

Transfection is also a key step in producing large quantities of nucleic acids and proteins. For example, transformation has long been used to propagate and amplify DNA in bacterial host. By introducing a gene into bacteria, large quantities of the protein encoded by the gene can also be produced. The proteins thus obtained are valuable for both research and therapeutic applications.

By stably expressing an exogenous gene into cells, one can change the properties and functions of the cells. These cells may then be used for therapeutic applications. For example, somatic cells removed from a patient with a defective gene can be transfected with a correct version of the same gene. Replacement of the transfected cells back into the patient may improve the patient's condition. This approach has been particularly successful in introducing genes into lymphocytes. Examples of transfection for gene therapy and some other applications can be found in publications by Bordignon et al. and Dick et al. (Science 270:470-475, 1995 and Blood 78:624-634, 1991 respectively) which are hereby incorporated by reference.

Biological reagents may be introduced into prokaryotic cells and some eukaryotic cells with varying degrees of ease. For example, heat shock method is routinely used to transfect DNA into bacteria and yeast. However, it is more difficult to introduce DNA into eukaryotic cells, such as human cells. Some sophisticated methods have been designed for this purpose and many improvements are used to increase transfection efficiency.

One way to introduce biological reagents into cells is by direct microinjection. Although it is difficult to introduce reagents into a large number of cells by this method, microinjection is useful for delivering reagents into some special cells, such as oocytes, skeletal muscles and neurons, which may be resistant to other transfection methods. Microinjection is also valuable when the number of target cells available is limited.

Biological reagents can also be introduced into cells by particle bombardment. In this method, microscopic particles, coated with the reagents to be transfected, are accelerated by a shock wave in a gaseous medium so that the particles are able to penetrate cells and deliver the reagents thereto. The shockwave may be produced by a variety of means including high-voltage electrical discharge (see McCabe et al., Bio/Technology 6, 923, 1992; U.S. Pat. No. 5,149,655) or helium pressure discharge (see Williams et al., Proc Natl Acad Sci USA 88, 2726, 1991).

DNA uptake by cells can be enhanced by facilitators such as calcium phosphate and diethylaminoethyl (DEAE)-dextran. Treatment with either of these chemicals is thought to produce an environment that promotes the attachment of DNA (presumably in complex with either calcium phosphate or DEAE-dextran) to the cell surface and subsequent endocytosis. DEAE-dextran is especially useful for transient transfection (Gonzalez A. L., et al. Trends Genet. 11:216-7, 1995). The original protocol for calcium phosphate transfection was described by Graham and van der Eb (Virology, 52: 456-467, 1973). This method was modified by Wigler et el. (Proc. Natl. Acad. Sci., 76: 1373-1376, 1979) and by Chen and Okayama (Mol. Cell. Biol., 7: 2745-2752, 1987).

Artificial membrane vesicles (liposomes) are useful delivery vehicles in vitro and in vivo. Most of these procedures involve encapsulation of DNA or other molecules with liposomes, followed by fusion of the liposomes with the cell membranes (Hofland, H. E .J., et al., Proc. Natl. Acad. Sci. USA 93: 7305-7309, 1996; Gao, X., and Huang, L., Biochem. 35:1027-1036, 1996; Liu, Y., et al., J. Biol. Chem. 270: 24864-24870, 1995). DNA are usually complexes with cationic substances, which may include cationic lipids, cationic polyamino acids (e.g., poly-L-lysine and polyomithine), cationic amphiphiles and polyethyleneimine. Examples of using cationic lipids for transfection are found in U.S. Pat. Nos. 5,616,745 and 5,851,818, which are hereby incorporated by reference.

Application of one or several short and sufficiently strong electric pulses to a suspension or monolayer of target cells may break down some parts of the cell membranes to form minute pores. Surrounding molecules can then diffuse or are driven into the target cells during the time when the cell membranes remain permeable to these molecules. This process is called electroporation. Methods of using electroporation to transfect cells can be found in the publication by Shigekawa and Dower (BioTechniques, Vol. 6: 742-751, 1988) and U.S. Pat. Nos. 4,910,140 and 4,750,100; which are hereby incorporated by reference. Electroporation is used to transfect both cells in suspension and cells adhering on a solid support. The method of electroporating cells adhering on a solid support can be found in Yang, et al., Nucleic Acid Research, Vol. 23, p2803-2810, 1995; and in Firth et al., BioTechniques 23:644-646, 1997.

Viruses derived from different sources are used for introducing genes into target cells. For example, bacterial phages have long been used in making DNA libraries in bacteria. Several widely used viral vectors for gene transfer into mammalian cells are derived from retroviruses (Miller, A. D., 1990, Human Gene Ther. 1:5-14) and adenovirus. Adenovirus vectors have been utilized for gene therapy and for gene expression in highly differentiated cells such as neuronal cells. Viral particles can be deposited on a solid support to increase the contacts between the particles and target cells, and thus the infection efficiency (see U.S. Pat. No. 5,811,274.).

In conventional methods, transfection is usually performed to deliver a homogenous biological reagent into one type of homogenous cells. Even if transfection is performed to introduce more than one reagent into cells, after transfection, the cells that contain a specific reagent are not known without further identification. One such example is the preparation of cDNA, genomic or expression libraries in bacteria. Screening is required to identify the cells expressing a specific DNA or protein. Library screening is feasible for identifying one or few cell groups, each of which expresses a reagent of interest. But when the effects of many transfected reagents on the cells are to be studied, the conventional methods are inadequate. A method is therefore needed to transfect multiple reagents into cells in such a manner that the cells containing each of the transfected reagents can be quickly and easily identified and examined.

Cell staining is a versatile technique widely used in research and diagnostics to demonstrate the presence of specific antigenic determinants on cells or tissues and to quantify the numbers of cells bearing particular determinants in a heterogeneous population (See Harlow and Lane, Antibodies, a laboratory manual, Cold Spring Harbor Press, 1988). The first step in a standard staining protocol is to attach cells to be stained to a solid support. Adherent cells may be grown on microscope slides, coverslips, or other optically suitable materials. Suspension cells can be handled in a suspension or centrifuged onto a solid support and bound to the support using chemical linkers. The second step is to fix and permeabilize the cells to expose the antigen. The cell preparations are then incubated with antibodies and washed to remove unbound antibodies.

Recently developed tissue arrays allow the staining of many different cells with one or few (usually no more than two) different antibodies (Kononen J, et al., Nature Medicine, 4:844-7, 1998). For some other applications, such as to screen proteins having a particular subcellular localization, cells must be stained with antibodies against a large number of different proteins. Most of the current methods only allow cell staining with less than a few antibodies at a time. Therefore a new method of staining cells is needed for such purposes.

SUMMARY OF THE INVENTION

The invention provides novel arrays of biological reagents and methods of making and using these arrays of biological reagents. These arrays are especially suitable for transfecting cells and staining cells with antibodies and for hybridization. In one embodiment of the method for making the arrays, capillary tubes are filled with the biological reagents of interest and bundled together in a defined order, so that each capillary tube with a specific reagent can be identified by the position among the bundles. For certain applications, the bundles of capillary tubes are further cut across sections to produce many arrays of reagents with predetermined heights.

The invention further includes methods for using the arrays of the invention to introduce a large number of different biological reagents into target cells. Each reagent is introduced into a specific subset of cells at a pre-defined position. In one embodiment of the method, a plurality of biological reagents are first arrayed and immobilized in a defined order; then the array of biological reagents is contacted with the target cells. Application of a certain condition to the cells results in that one or more of the reagents is introduced into a subset of target cells at a unique defined position.

Transfection can be a quick process, finished in less than a second (such as electroporation) and may require no further process (such as washing). Accordingly, arrays of weakly immobilized molecules can be used in transfection assays.

The invention also provides a method, using specially designed arrays to stain cells with a large number of different antibodies, with each antibody staining a subset of cells at a specific pre-defined position. In one embodiment of the method, a plurality of antibodies are first arrayed and immobilized in a defined order; then the antibody array is contacted with the target cells to allow the antibodies to bind their respective antigens.

A preferred embodiment of the array of the invention, for bringing two or more reagents in contact with one or more biological targets, generally comprises: one or more reagents; and one or more barriers adapted to at least temporarily maintain said reagents in at least one arrangement of two or more reagent portions so that said portions do not commingle with each other, wherein each said portion is maintained at a pre-defined locale in said arrangement so that each of said portions is adapted to be brought into contact with one or more biological targets, wherein the array preferably comprises at least two or more reagents wherein at least one of said reagent portions comprises all or part of two or more reagents.

One or more of said reagents is selected from a group consisting of DNA, RNA, antibodies, peptides, proteins, enzymes, carbohydrates, oligonucleotides, recombinant vectors, drugs, viruses, bacteria, mammalian cells, small organic molecules, and large organic molecules.

One or more of said barriers may comprise one or more at least partial capillary tubes, wherein one or more of said capillary tubes is made of at least one material selected from a group consisting of plastic, glass, nitrocellulose, nitrobenzyloxymethyl cellulose, aminobenzyloxymethyl cellulose, aminophenylthioether cellulose, diethylaminoethyl cellulose, and polyvinylidene fluoride.

Capillary tubes of varying diameters may be used including but not limited to diameters between 10 µm and 1 cm in varying numbers of capillary tubes, preferably between 10 and 100,000 tubes and more preferably between 100 and 10,000. The arrangement of reagent portions preferably comprises one or more cross-sectional slice of a plurality of capillary tubes. The height of the slices may vary including heights between but not limited to heights between 1 µm to 1 cm and more preferably between 10 µm to 1 cm.

One or more of the reagents may be immobilized among said barriers using one or more carriers comprising one or more components selected from a group consisting of cellulose, carbolynmethylcellulose, agarose, dextran, polyaminopolystyrene, polylysine, polyacrylamides, and derivatives thereof.

Two or more of said reagent portions of the array of the invention are preferably adapted to be brought simultaneously into contact with two or more predefined, biological targets, wherein one or more of said reagent portions is adapted to transfect one or more of said reagents into one or more predefined, biological targets and/or wherein one or more of said reagent portions is adapted to stain one or more predefined, biological targets.

One or more of said barriers of the array may, alternatively or in addition to the capillary tubes, comprise one or more supports having at least one substantially level surface comprising a plurality of spaces surrounding and between said reagent portions wherein said reagent portions are maintained at said predefined locations so that said portions do not commingle, wherein one or more of said supports is preferably made of at least one material selected from a group consisting of plastic, glass, nitrocellulose, nylon, polyvinylidene fluoride, and metal. One or more of said supports comprises one or more solid supports selected from a group consisting of rigid glass plates, rigid plastic plates, nitrocellulose membranes, nylon membranes, polyvinylidene difluoride membranes, metal membranes, and porous membranes.

One or more of said supports also preferably comprise a layer of one or more polymers adapted to immobilize one or more of said reagents, wherein one or more of said polymers is selected from a group consisting of polylysine and polyethyleneimine.

A preferred method of the invention for making one or more arrays for bringing one or more reagents in contact with two or more biological targets generally comprises the steps of, providing one or more reagents; and providing one or more barriers adapted to at least temporarily maintain said reagents in at least one arrangement of two or more reagent portions; immobilizing said reagent portions in said arrangement so that said portions do not commingle with each other, whereby each said portion is maintained at a predefined locale in said arrangement so that each of said portions is adapted to be brought into contact with one or more predefined, biological targets.

In applications in which one or more of said barriers comprises one or more at least partial capillary tubes, the step of immobilizing preferably comprises the steps of, introducing one or more of said reagents into said capillary tubes; and bundling said capillary tubes in said predefined arrangement, wherein the method may further comprise the step of cutting said bundled capillary tubes into a plurality of cross-sectional slices.

The step of introducing may comprise the steps of, mixing one or more of said reagents with one or more carrier solutions; placing said mixture of reagents and carrier solution into one or more of said capillary tubes; and at least partially solidifying said mixture until said mixture is substantially immobile. The method may also further comprise the step of cutting said bundled capillary tubes into a plurality of cross-sectional slices.

One or more of said capillary tubes used in the method to make the array of the invention is preferably made of at least one material selected from a group consisting of plastic, glass, nitrocellulose, nitrobenzyloxymethyl cellulose, aminobenzyloxymethyl cellulose, aminophenylthioether cellulose, diethylaminoethyl cellulose, and polyvinylidene fluoride, wherein one or more of said arrangements preferably comprises between 10 to 100,000 capillary tubes, and more preferably at least 10,000 capillary tubes.

One or more of said reagents used in the method are preferably immobilized among said barriers using one or more carriers comprising one or more components selected from a group consisting of cellulose, carbolynmethylcellulose, agarose, dextran, polyaminopolystyrene, polylysine, polyacrylamides, and derivatives thereof.

Alternatively or in addition to the capillary tubes, one or more of said barriers may comprise one or more supports having one or more substantially level surface comprising a plurality of spaces surrounding and between said reagent portions wherein said reagent portions are maintained at said predefined locations so that said portions do not commingle; and wherein said step of immobilizing comprises the step of depositing one or more of said reagents onto one or more of said surfaces, and wherein said step of immobilizing may further comprise the steps of, pretreating one or more of said surfaces by applying one or more layers of one or more polymers, adapted to interact with one or more of said reagents. One or more of the polymers may be selected from a group consisting of polylysine and polyethyleneimine and one or more of said supports is made of at least one material selected from a group consisting of plastic, glass, nitrocellulose, nylon, polyvinylidene fluoride, and metal; and further, wherein one or more of said supports comprises one or more solid supports selected from a group consisting of rigid glass plates, rigid plastic plates, nitrocellulose membranes, nylon membranes, polyvinylidene difluoride membranes, metal membranes, and porous membranes.

The reagents used in the method to make the array of the invention may be selected from a group consisting of DNA, RNA, antibodies, peptides, proteins, enzymes, carbohydrates, oligonucleotides, recombinant vectors, drugs, viruses, bacteria, mammalian cells, small organic molecules, and large organic molecules.

A preferred method of the invention for bringing the reagents in contact with one or more biological targets generally comprises the steps of, providing an array comprising, one or more reagents; and one or more barriers adapted to at least temporarily maintain said reagents in at least one arrangement of two or more reagent portions so that said portions do not commingle with each other, wherein each said portion is maintained at a predefined locale in said arrangement so that each of said portions is adapted to be brought into contact with one or more biological targets; providing one or more biological targets; designating an address to each reagent portion based on said predefined locale and an address to each of said predefined, biological targets; corresponding at least one of said reagent portions to at least one of said biological targets based on said designated reagent portion and biological target addresses; contacting said predefined reagent portions with their respective corresponding biological targets, whereby some or all of each specific reagent portion is transferred to said specific reagent portion's corresponding biological target. In the case of hybridization, the target is transferred to the reagent portion.

The array preferably comprises at least two or more reagents, wherein at least one of said reagent portions comprises all or part of two or more reagents, wherein one or more of said reagents is selected from a group consisting of DNA, RNA, antibodies, peptides, proteins, enzymes, carbohydrates, oligonucleotides, recombinant vectors, drugs, viruses, bacteria, mammalian cells, small organic molecules, and large organic molecules.

One or more of said barriers comprises one or more at least partial capillary tubes and preferably comprises a plurality of bundled capillary tubes and more preferably comprises one or more cross-sectional slices of the plurality of bundles capillary tubes.

Alternatively or additionally, method may further include removing the reagents from the capillary tubes and fixing the reagents to one or more supports having at least one substantially level surface comprising a plurality of spaces surrounding and between said reagent portions wherein said reagent portions are maintained at said predefined locations so that said portions do not commingle, wherein one or more of said supports may comprise one or more solid supports selected from a group consisting of rigid glass plates, rigid plastic plates, nitrocellulose membranes, nylon membranes, polyvinylidene difluoride membranes, metal membranes, and porous membranes. One or more of said supports comprise a layer of one or more polymers adapted to immobilize one or more of said reagents. The reagents may be fixed to the supports using affinity absorption or electrophoresis.

The step of providing two or more biological targets may comprise the step of seeding and adhering two or more target cells on one or more cell growth supports.

The step of contacting said predefined reagent portions with their respective corresponding biological targets, whereby some or all of each specific reagent portion is transferred to said specific reagent portion's corresponding biological target, may alternatively or additionally comprise the step of, seeding and adhering one or more of said biological targets on said biological targets' corresponding predefined reagent portions.

The contacting step may also comprise the step of applying one or more conditions to one or more of said reagent portions to facilitate said transfer of some or all of each specific reagent portion to said specific reagent portion's corresponding biological target, wherein said step of applying one or more conditions may comprises the step of applying one or more electric pulses to one or more of said reagent portions.

BRIEF DESCRIPTION OF THE DRAWINGS

FIG. 1 is a schematic view of a preferred method for making the preferred embodiment of the array of the invention;

FIG. 2 is an example of transfection using a preferred method of using an array of the invention; and FIG. 3 is an example of staining using a preferred method of the using an array of the invention.

DESCRIPTION OF THE PREFERRED EMBODIMENTS AND METHODS

The invention relates to novel arrays of biological reagents and methods for making and using the arrays to transfect and/or stain biological targets. In one preferred embodiment, capillary tubes are used to facilitate arraying and immobilizing reagents. The transfection methods of using the arrays generally include the steps of making an array of a plurality of biological reagents; contacting the array with target cells; and exposing the cells under certain conditions, such as electroporation, to allow the reagents to enter the target cells. After transfection, most of the reagents will be introduced into the target cells, each one into a subset of the cells at a pre-defined position. In another embodiment, an array of antibodies is used to stain cells so that each of the antibodies binds to its specific antigens in cells at specific positions.

The arrays of biological reagents, prepared in accordance with the invention, are particularly useful for introducing a large number of different biological reagents into cells and for staining cells with a large number of antibodies. The arrays and methods are useful for other applications including, but not limited to, DNA hybridization assays using DNA arrays and protein binding assays using protein arrays. In each of these applications, the arrays are brought into contact with the biological targets. The term "biological target" includes any materials of biological interest and includes, but is not limited to, peptides, proteins, antibodies, oligonucleotides, DNA, RNA, proeukaryotic cells, eukaryotic cells and mammalian cells.

The term "biological reagents" or "reagents" is used herein, for purposes of the specification and claims, to mean any material of biological relevance. They include, but are not limited to, peptides, proteins, antibodies, enzymes, carbohydrates, oligonucleotides, DNA, RNA, recombinant vectors, drugs, viruses, bacteria, mammalian cells, small organic and inorganic molecules. Many methods are available to produce a large number of biological reagents: oligos, peptides small organic and inorganic chemicals can be obtained through chemical synthesis (see The Combinatorial Index, edited by B. A. Bunin, Academic Press, 1998); DNA (including cDNA), RNA (including MRNA) and recombinant proteins can be obtained through molecular biology techniques (such as those reviewed in Sambrook et al., Molecular Cloning, a laboratory manual, Cold Spring Harbor Press, 1989); polyclonal and monoclonal antibodies can be produced by standard techniques in animals such as mouse, rabbits, goats and chickens (See Harlow and Lane, Antibodies, a laboratory manual, Cold Spring Harbor Press, 1988), or produced by recombinant DNA techniques (see Kipriyanov and Little, Mol Biotechnol, 12:173-201, 1999).

In the preferred embodiment of the array, capillary tubes are used as barriers between reagent portions to facilitate arraying and immobilizing biological reagents. The use of capillary tubes ensures that weakly immobilized biological reagents will not diffuse laterally to other positions. The term "capillary tube" is used herein, for purposes of the specification and claims, to mean any enclosed elongated structure capable of containing and supporting biological reagents. The tube typically has a cylindrical internal shape, although other shapes, such as triangular, rectangular, square, or any other shapes can be used, depending on applications and other considerations. The arrays of capillary tubes may be cut or sliced by several methods, including those used to prepare frozen or paraffin tissue sections. The capillary tubes may be made from materials that do not interfere with transfection or binding assays, such as plastic, glass, nitrocellulose, nitrobenzyloxymethyl cellulose, aminobenzyloxymethyl cellulose, aminophenylthioether cellulose, diethylaminoethyl cellulose, and polyvinylidene fluoride.

Capillary tubes are first filled with biological reagents. The biological reagents can be injected into capillary tubes by positive pressure (e.g., with a syringe) or moved into the capillary tubes by surface tension or negative pressure (e.g., with a peristaltic pump). In addition to biological reagents, other materials, that facilitate immobilization or subsequent applications, may also be included when filling the capillary tubes. Such materials include, but are not limited to, microparticles and various cationic substances.

A biological reagent is usually introduced into a capillary tube as liquid solution. After introduction, the reagent solution becomes solidified and immobilized. A carrier solution is preferably used to facilitate the introduction of the reagent into the tube. "Carrier solution" or "carrior" is used herein, to mean a monomer and/or polymer solution that can be applied as liquid to a capillary tube and converted to a solid polymer by adding a polymer initiator or by irradiation such as UV or IR radiation. The carrier solutions may comprise, but are not limited to, cellulose, carbolynmethylcellulose, agarose, dextran, polyaminopolystyrene, polyacrylamides and their derivatives. In one preferred embodiment, the biological reagents are mixed with low melting agarose gel and introduced into the capillary tube while the gel is in liquid form. After filling, the temperature is lowered to solidify the gel and immobilize the reagants in the capillary tube. In another embodiment, the biological reagents are mixed with acrylamide solution and polymerized by adding N,N,N',N'-Tetramethylethylenediamine.

The immobilization strength may vary depending on a given application. For the purpose of binding assays, such as nucleic acid hybridization and protein-protein binding, the interactions between biological reagents, carrier and capillary tubes should be strong enough to withstand multiple washes. Such strong interactions are usually achieved through covalent or strong non-covalent bonds. An example of covalent immobilization of nucleic acids and proteins by co-polymerization is described by Vasiliskov et la., (BioTechniques 27:592-606, 1999). For the purpose of transfection, weak interaction is applicable. For example, the reagents may be embedded in agarose or polyacrimide polymers to transfect by electroporation. In some applications, DNA is immobilized by binding to positively charged polymers, such as polylysine. Other methods are known in the field for immobilizing proteins and nucleic acids (e.g. Ternynck, T., Avrameas, S., FEBS-Letters 23, 24-28, 1972; Guesdon, J. L. et al, J. Immunol. Meth. 21,59-63, 1978).

A plurality of capillary tubes filled with biological reagents are then bundled together in a predefined order, so that each capillary tube with a specific reagent can be identified by its position among the bundles. FIG. 1 is a schematic view of this method of making a preferred embodiment of the array. As shown in FIG. 1, the capillary tubes are filled with one or more biological reagents. The tubes are bundled together so that the tubes are located at a predetermined position in the bundle. The bundle of tubes is then cut into cross-sections to produce arrays of any desired height. The order of the steps of filling the tubes and bundling the tubes together are not critical and will depend on a given application and the reagents used. The number of bundled capillary tubes may vary from a few up to many thousands, depending on the diameters of the capillary tubes and the total area of the bundled capillary tubes, which in turn depends on the given application. For example, the diameters preferably range from 10 μm to 1 mm and the number of tubes ranges from 10 to 100,000, preferably from 100 to 10,000. For example, uniform capillary tubes with a diameter of 0.5 mm, 1600 capillary tubes will fit in a 2 cm×2 cm square area. Ten thousand (10,000) capillary tubes with a diameter of 0.2 mm will fit in a square area of 2 cm×2 cm. The capillary tubes may be glued or otherwise bundled together for easy handling.

The diameter of each capillary tube may vary from less than a few micrometers to several millimeters. All capillary tubes may have the same diameter or different diameters. For example, some of the capillary tubes may have different diameters so that they can be used as markers to denote the positions of other capillary tubes.

Each capillary tube may be filled with only one type of reagent, or with more than one type of reagents. For example, when each capillary tube has two kinds of reagents, one kind may be the same for all capillary tubes while the other is different for each tube. The reagent present in all capillary tubes may be used as a marker to monitor transfection efficiency or conditions or as an expression vector containing a specific gene, such as an apoptotic gene for use in screening potential anti-apoptotic genes. Furthermore, each capillary tube may contain a different combination of reagents or each capillary tube may contain DNA or proteins from different biological sources such as different patients.

The heights of the capillary tubes may be varied, from micrometers to meters, e.g. between 1 µm to 1 cm., preferably between 10 µm to 1 cm. For some applications, the bundles of capillary tubes are preferably cut across sections to form arrays of reagents with heights ranging from micrometers to centimeters. Arrays with heights of micrometers are suitable for nucleic acid hybridization and protein binding assays. For transfection assays, the section may range from micrometers to centimeters, depending on the transfection apparatus configurations.

The array of capillary tubes may be cut or sliced by several methods, including those used to prepare frozen or paraffin tissue sections. For example, devices similar to Vibratome® from Energy Beam Sciences Inc. may be used to prepare array sections. Prior to cutting, the array of capillary tubes may be cooled or heated to facilitate cutting. By repeating the cutting process, many arrays may be produced.

In another preferred embodiment of the method, prior to filling the capillary tubes with biological reagents, a plurality of capillary tubes are first bundled together and then each capillary tube, at a predefined position, is filled with one or more kinds of biological reagents. In another embodiment, instead of bundling the capillary tubes together, capillary tubes may be formed in blocks of solid material, e.g., by drilling. If necessary, arrays made by this latter method may also be further cut into thin sections, to produce many arrays of biological reagents.

The arrays of biological reagents made by the above methods may be extracted from or otherwise taken out of the capillary tubes and then placed and glued or otherwise transferred and immobilized on flat solid supports, such as glass or filters, for the purpose of easy handling and storage. The solid supports can be made from electric conducting materials such as metal or porous membranes. The array of reagents removed from the tubes may be transferred and immobilized on the support by affinity absorption and/or facilitated by electrophoresis. For example, the transfer of an array of DNA, made using the above described capillary tube method, onto a nylon membrane may be facilitated using electrophoresis. The positions of all the reagents will be retained.

Rigid capillary tubes are helpful in immobilizing and arraying biological reagents. However, in some other instances, biological reagents can be directly immobilized in a medium, in the shape of rod; then the rod-shaped reagents may be bundled in a defined order and cut into sections.

The methods of the invention for transfection may also utilize arrays made up of a plurality of reagents that are deposited onto a flat solid support, one or few reagents at a time, so that the reagents are located at predefined positions.

The term "solid support" is used herein, to mean the structure on which arrays of biological agents are placed. The supports may comprise rigid plates (glass or plastics) and/or membranes made of nitrocellulose, nylon, or polyvinylidene difluoride (PVDF). The solid supports can be made from electric conducting materials such as metal or porous membranes. Several techniques for depositing a plurality of oligonucleotides, cDNA, proteins and other biological reagents are described by Lehrach, et al. (Hybridization fingerprinting in genome mapping and sequencing, genome analysis, Vol 1, Davies and Tilgham, Eds, Cold Spring Harbor Press, pp. 39-81, 1990) and Brown et al. (U.S. Pat. No. 5,807,522).

The solid supports are preferably pretreated so that biological reagents deposited on them can be immobilized with adequate strength suitable for transfection. For example, the solid supports may be coated with one or more layers of polymers that in turn will interact with biological reagents through non-specific, non-covalent bonds. For example, polymers comprising polylysine or polyethyleneimine may be used to coat glass slides or coverslips for immobilizing nucleic acids and cell cultures.

As noted, arrays of biological reagents prepared in accordance with the invention are particularly useful for introducing a large number of different biological reagents into cells and for staining cells with a large number of antibodies. The arrays and methods are useful for other applications including, but not limited to, DNA hybridization assays using DNA arrays and protein binding assays using protein arrays.

The invention also provides methods for using arrays of biological reagents to transfect a large number of biological reagents into target cells. Transfection is performed so that each biological reagent is transfected into a subset of the target cells at one or more unique specific positions. The method comprises three basic steps. First, the biological reagents to be transfected are arrayed and immobilized, each reagent at a predefined position. Second, target cells are prepared and contacted with the array of biological reagents. The contacts are made so that each of the reagents is contacted with a subset of the target cells and the position of the subset cells contacting a specific reagent can be determined. Third, a condition is applied if needed to allow all or some of the biological reagents to enter the target cells.

The term "transfection" is used herein to mean introducing or loading reagents into biological targets. As previously noted, other terms are also used to denote some special processes of transfection. For example, transformation sometimes refers to the process of introducing a piece of DNA, usually via a vector, into bacteria; and infection refers to the process of delivering nucleic acids into cells by viruses.

The purpose of most DNA transfection is to produce the proteins encoded by the DNA in the target cells. For this purpose, the DNA is usually placed in expression vectors. A variety of vectors have been developed to express genes in eukaryotic cells (Sambrook et al., Molecular Cloning, a laboratory manual, Cold Spring Harbor Press, 1989) and some technologies allow simple transfer of DNA segments from non-expression vectors to expression vectors (U.S. Pat. No. 5,888,732).

The first step of the method is to make arrays of reagents. The arrays to be used in transfection preferably have at least two features: first, each biological reagent has a unique position and can be identified later by this position; second, the biological reagents can be released from array supports and enter the target cells during transfections. Currently available DNA arrays are not useful for transfection because these DNA arrays generally employ strong immobilization, such as covalent or very strong multivalent non-covalent bonds between biological reagents and solid supports. To enter the cells during transfection, biological reagents must first break away from their solid supports. Some transfection methods, such as electroporation, can be a quick process, finished in less than a second. Transfections may require no further process, such as washing, which is usually necessary for protein and nucleic acid binding assays. As such, arrays of weakly immobilized molecules are preferably used in transfection. However, strong immobilization may still be utilized in the present method as long as the biological reagents can be released from the solid support to enter the target cells during transfection.

In the second step of the transfection method, target cells are prepared and contacted with arrays of biological reagents. The transfection target may include one or many cells. The target cells are the cells of choice in a specific assay. For example, in a transfection assay, target cells are the cells into which the biological reagents are to be introduced. Depending on the application, target cells can be any type of cells, such as bacteria, yeast, plant cells, animal cells, mammalian cells, or cells of human origin. Cultured cells (cell lines or primary cells) or cells in the form of tissues or tissue sections can be used.

In one preferred method, target cells are first seeded on a cell growth support and adhere to it. A cell growth support is a solid structure on which cells are able to attach and grow. Any means of directing the target cells to the cell growth support may be used while ensuring that transfection can occur. For example, target cells can naturally attach to a cell growth support by gravitation or centrifuge. Alternatively, the target cells may be filtered onto a porous cell growth support as fluid, containing the target cells, flows through the support. A porous support is a thin filter made of synthetic or natural materials that are compatible with cell growth and transfection, including nitrocellulose, cellulose esters, polyethylene terephthalate, polystyrene or polycarbonate. Supports may also be coated with any material compatible with transfection, such as collagen and polycations. Polycations include, for example, polybrene, protamine and polylysine. An embodiment of a porous cell growth support is the bottom surface of a cell culture cup such as Costar Transwell insert, Falcon cell culture insert, Nunc Anopore and polycarbonate TC insert, or Millipore Millicell insert. Cells can be cultured on the support for certain lengths of time, from hours to days, before the transfection. Incubation will allow cells to spread out and attach securely to the supports.

Target cells on a growth support are then contacted with one or more arrays of biological reagents. The contacts are made with reasonable strength without damaging cells or arrays. It is important to preserve the positional information of each biological reagent so that the cells contacting with a reagent can be identified by a specific position or address. Several methods can be employed to preserve such information. For example, the positional information will be preserved if the array and the cell growth support are precisely aligned. Or, the arrays can be specially designed so that some positions of the arrays contain markers which will be introduced into cells during transfection. After transfection, cells containing the markers will show the positions of the cells transfected with other reagents. Any detectable materials different from the transfected reagents can be used as markers, such as enzymes (e.g., horseradish peroxides, alkaline phosphatase and beta-galactosidase) and fluorescent molecules (e.g., green fluorescent protein, fluorescent dextran and fluorescent microbeads). Each of the above methods effectively assigns addresses to both the reagent portion locations and the locations of their corresponding targets.

In another preferred method, target cells are seeded directly on top of an array. That is, the solid support on which biological reagents are arrayed and immobilized is also the cell growth support. Since each of the biological reagents is immobilized at a specific predetermined position on the support, cells at a specific location are contacted only with the reagents immobilized there.

In a preferred third step of the method, a condition may be applied to the targets and arrays to promote the transfer of the biological reagents into the targets. For example, in instances where the biological reagent includes a virus, such as virus particles used to delivery DNA, RNA or proteins, the transfer may be promoted by incubating the arrays of reagents with the target cells for a certain length of time to facilitate viral infection. Other conditions may include, but are not limited to, heat shock, electroporation, treatment with liposomes, and pressure and chemical stimulation.

In another preferred method, the target cells are seeded on an electrically conducting support and the array of biological reagents is also electrically conducting. The electrically conducting support can be a metal plate or a porous membrane, such as a filter membrane. Electroporation is used to introduce the biological reagents into the target cells. The electroporator is preferably specially designed for this use to achieve maximum effect. However, commercial electroporators such as Gene Pulser™ from Bio-Rad Inc may also be used. The effective voltage varies from less than a hundredth of a volt to several thousand volts, depending on several factors including cell type, reagent types, medium types and transfection configurations. For example, to electroporate DNA into cells, the cell support is connected to the positive electrode of an electroporator and the array of DNA is connected to the negative electrode of the electroporator. The connections should deliver a uniform electric field.

To further facilitate transfection, several methods can be used to accelerate the release of biological reagents from the solid support. The reagents may be released thermodynamically or electrodynamically. If the reagents are immobilized through chemical bonds, they may also be released by breaking the bonds, for example by enzyme digestion.

After transfection, if necessary, targets are separated from the arrays of reagents. Transfected targets are then kept under appropriate conditions to allow the targets to survive and characterized. Subsequently, numerous assays can be performed to examine the transfected targets.

Non-adherent cells are preferably transfected by the methods of the invention after being immobilized in a medium such as soft agar.

By using the transfection methods described above, thousands of biological reagents, such as proteins, antibodies, and/or cDNA clones, can be simultaneously transfected into cells, and their activities and effects on cells can be quickly examined. Therefore, the method has numerous applications in research, drug screening, clinical diagnosis and many other areas. For example, when different proteins are transfected into cells, the effect of each of these proteins on cells can be rapidly examined. Similarly, when different nucleic acids are transfected into cells, the properties and functions of their encoded proteins can be evaluated quickly for each of the nucleic acids. The methods presented here can be used to screen genes that play important roles in many cellular processes, such as screening cell death genes, anti-apoptotic genes, oncogenes and tumor-suppresser genes. The methods can also be used to produce cells with desired phenotypes. For example, cells can be transfected with different genes and then cells exhibiting the desired phenotype can be subsequently selected.

The invention also provides methods for staining cells with a large number of antibodies. The term "staining" is used herein to include the process of binding antibodies to their respective antigens present in the cells for the purpose of revealing the antigens. Other terms such as "immunostaining" and "immunohistochemical staining" are included within term "staining."

For example, staining may be performed so that each antibody stains a subset of the target cells at one or more unique specific positions. This method generally comprises three steps. First, a large number of antibodies are arrayed and immobilized, each at a predefined position. Second, target cells are prepared and contacted with the antibody array. The contacts are made so the each of the antibodies is contacted with a subset of the target cells and the position of the subset cells contacting a specific antibody can be determined. Third, antibodies specifically bind their respective antigens present in the target cells.

In one preferred embodiment of the antibody array, a plurality of antibody reagents are deposited onto a flat solid support, so that each antibody reagent is located at predefined position. The solid supports are preferably pretreated so that biological reagents deposited on them will have an immobilization strength suitable for staining. One method for treating the solid support is to coat the support with a layer of one or more polymers that, in turn, will interact with antibodies. The strength of the interactions is preferably substantially weaker than that between antibodies and their antigens. For example, a mutant of protein A, with decreased affinity for antibodies, may be used to coat solid supports. In another preferred embodiment of an antibody array, capillary tubes are used.

EXAMPLES

The following examples illustrate, but in no way are intended to limit the invention.

Example 1

One hundred (100) capillary tubes were filled with DNA, all of which comprise sequences encoding a green fluorescent protein. The capillary tubes were 2 mm in outer diameter, about 0.2 mm thick, and about 1 cm high. The DNA was first mixed with low melting agarose gel and introduced into the capillary tubes by injection using syringes. After the gel solidified, the capillary tubes were bundled together.

Example 2

The DNA array made in EXAMPLE 1 was cut into cross sections to produce arrays 0.2 mm high. The height of the array sections can be varied, from less than a micrometer to more than a centimeter, depending on the application. The sections were placed on an aluminum support and stored at 4° C. before use.

Example 3

The DNA array made in EXAMPLE 2 was used to transfect COS7 cells. Cells were seeded on a porous support (a cell culture insert). The DNA array on the aluminum support was contacted with the cells. The aluminum support was connected to an electroporator (Bio-Rad Gene Pulser™) through a negative electrode plate while the cell growth support was connected through a positive electrode plate. An electric pulse of 250 volts and a time constant of 2 milliseconds was delivered. Since all DNA encoded a green fluorescent protein, transfected cells were revealed under fluorescent microscope as shown in FIG. 2. The cells at dozens of locations were transfected with DNA.

Example 4

In this example, expression vectors encoding a green fluorescent protein were transfected into COS7 cells at different locations. First, a clean sterile coverslip was coated with poly-L-lysine by incubating in 1 mg/ml poly-L-lysine (in distilled water) for 15 minutes, followed by a wash with sterile water. Vector DNA were then immobilized on the coverslip at twenty different pre-defined locations. COS7 cells were seeded on top of the coverslip in a tissue culture dish. After 12 hours, Lipofectin™ (see, Felgner, J., et al., Proc. Natl. Acad. Sci. USA 84:7413-7417, 1987) was added to facilitate the uptake of DNA into the cells. Eighteen (18) hours after transfection, cells were examined under fluorescent microscope and found to express fluorescent protein at several distinct locations.

The COS7 cells were readily transfected using the arrays and the invention methods. Additional mammalian cell lines have been similarly and successfully transfected using the methods and compositions according to the present invention. For example, 293T and Hela cells have been transfected with both DNA and antibodies. Other transfection methods such as calcium phosphate-mediated transfection, virus infection and particle bombardment may also be used.

Example 5

This example demonstrates the use of antibody arrays prepared using the method of the invention to stain cells. Antibodies to ten different proteins were used to make the antibody array. Each antibody was mixed with low temperature melting gel and injected into a plastic capillary tube 1 cm high, 2 mm in outer diameter and about 0.2 mm thick. After the gel solidified, the capillary tubes were bundled together and cut into cross sections to produce arrays of about 1 mm high. FIG. 3 shows E-cadherin staining at one position.

E-cadherin transfected L cells were seeded on a coverslip and cultured for two days until confluence. Then the cells were fixed and permeabilized in methanol/acetone for 10 minutes at −20° C. After rinsing with phosphate-buffered saline, the cells were contacted with the antibody array for about one hour. Cells were then separated from the array and rinsed with phosphate-buffered saline. Fluorescent-labeled secondary antibodies were then added for half an hour. After washing, the cells were observed under a microscope. Cells at several different positions were stained with antibodies to determine that there was little mixing of the antibodies, as evidenced by the distinct subcellular localizations of different antigens and the lack of staining at the borders of capillary tubes as shown in FIG. 3.

Although specific features of the invention are shown in some drawings and not others, this is for convenience only as some feature may be combined with any or all of the other features in accordance with the invention.

Other embodiments and modifications will occur to those skilled in the art and are within the following claims:

What is claimed is:

1. An array for bringing one or more reagents in contact with two or more biological targets comprising,
one or more reagents; and
one or more barriers adapted to at least temporarily maintain said reagents in at least one arrangement of two or more reagent portions so that said portions do not commingle with each other, wherein each said portion is maintained at a predefined locale in said arrangement so that each of said portions is adapted to be brought into contact with one or more predefined, biological targets.

2. The array of claim 1, comprising at least two or more reagents wherein at least one of said reagent portions comprises all or part of two or more reagents.

3. The array of claim 1, wherein one or more of said reagents is selected from a group consisting of DNA, RNA, antibodies, peptides, proteins, enzymes, carbohydrates, oligonucleotides, recombinant vectors, drugs, viruses, bacteria, mammalian cells, small organic molecules, and large organic molecules.

4. The array of claim 1, wherein one or more of said barriers comprises one or more at least partial capillary tubes.

5. The array of claim 4, wherein one or more of said capillary tubes is made of at least one material selected from a group consisting of plastic, glass, nitrocellulose, nitrobenzyloxymethyl cellulose, aminobenzlyoxymethyl cellulose, aminophenylthioether cellulose, diethylaminoethyl cellulose, and polyvinylidene flouride.

6. The array of claim 4, wherein said capillary tubes have diameters between 1 µm to 1 cm.

7. The array of claim 4, wherein one or more of said arrangements comprises between 10 to 100,000 capillary tubes.

8. The array of claim 4, wherein said capillary tubes have diameters between 1 µm to 1 cm.

9. The array of claim 4, wherein one or more of said arrangements comprises between 100 to 10,000 capillary tubes.

10. The array of claim 4, wherein one or more of said arrangements comprises a cross-sectional slice of a plurality of said capillary tubes.

11. The array of claim 10, wherein said capillary tubes of said cross-sectional slice have a height between about 1µm to 1 cm.

12. The array of claim 10, wherein said capillary tubes of said cross-sectional slice have a height between about 10µ to 1 cm.

13. The array of claim 1, wherein one or more of said reagents are immobilized among said barriers using one or more carriers comprising one or more components selected from a group consisting of cellulose, carbolynmethylcellulose, agarose, dextran, polyaminopolystyrene, polylysine, ployacrylamides, and derivatives thereof.

14. The array of claim 1, wherein two or more of said reagent portions are adapted to be brought simultaneously into contact with two or more predefined, biological targets.

15. The array of claim 1, wherein one or more of said reagent portions are adapted to transfect one or more of said reagents into one or more predefined, biological targets.

16. The array of claim 1, wherein one or more of said reagent portions is adapted to stain one or more predefined, biological targets.

17. The array of claim 1, wherein one or more of said barriers comprises one or more supports having at least one substantially level surface comprising a plurality of spaces surrounding and between said reagent portions wherein said reagent portions are maintained at said predefined locations so that said portions do not comingle.

18. The array of claim 17, wherein one or more of said supports is made of at least one material selected from a group consisting of plastic, glass, nitrocellulose, nylon, polyvinylidene fluouride, and metal.

19. The array of claim 17, wherein one or more of said supports comprises one or more solid supports selected from a group consisting of rigid glass plates, rigid plastic plates, nitrocellulose membranes, nylon membranes, polyvinylidene difluoride membranes, metal membranes, and porous membranes.

20. The array of claim 17, wherein one or more of said supports comprise a layer of one or more polymers adapted to immobilize one or more of said reagents.

21. The array of claim 20, wherein one or more of said polymers are selected from a group consisting of polylysine and polyethyleneimine.

22. A method for making one or more arrays for bringing one or more reagents in contact with two or more biological targets comprising the steps of,
    providing one or more reagents; and
    providing one or more barriers adapted to at least temporarily maintain said reagents in at least one arrangement of two or more reagent portions;
    immobilizing said reagent portions in said arrangement so that said portions do not comingle with each other, whereby each said portion is maintained at a predefined locale in said arrangement so that each of said portions is adapted to be brought into contact with one or more predefined, biological targets.

23. The method of claim 22, wherein one or more of said barriers comprises one or more at least partial capillary tubes, and wherein said step of immobilizing comprises the steps of,
    introducing one or more of said reagents into said capillary tubes; and
    bundling said capillary tubes in said predefined arrangement.

24. The method of claim 23, further comprising the step of cutting said bundled capillary tubes into a plurality of cross-sectional slices.

25. The method of claim 23, wherein said step of introducing comprises the steps of, mixing one or more of said reagents with one or more carrier solutions; placing said mixture of reagents and carrier solution into one or more of said capillary tubes; at least partially solidifying said mixture until said mixture is substantially immobile.

26. The method of claim 25, further comprising the step of cutting said bundled capillary tubes into a plurality of cross-sectional slices.

27. The method of claim 23, wherein one or more of said capillary tubes is made of at least one material selected from a group consisting of plastic, glass, nitrocellulose, nitrobenzyloxymethyl cellulose, aminobenyloxymethyl cellulose, aminophenylthioether cellulose, diethylaminoethyl cellulose, and polyvinylidene fluoride.

28. The method of claim 23, wherein one or more of said arrangements comprises between 10 and 100,000 capillary tubes.

29. The method of claim 23, wherein one or more of said arrangements comprises at least 10,000 capillary tubes.

30. The method of claim 22, wherein one or more of said reagents are immobilized among said barriers using one or more carriers comprising one or more components selected from a group consisting of cellulose, carbolynmethylcellulose, agarose, dextran, polyaminopolystyrene, polylysine, polyacrylamides, and derivatives thereof.

31. The method of claim 23, further comprising the steps of removing said reagent portions from said tubes and fixing said portion to one or more supports having one or more substantially level surfaces wherein said reagent portions are maintained at said predefined locations so that said portions do not comingle.

32. The method of claim 31, wherein said step of immobilizing further comprises the steps of, pretreating one or more of said surfaces by applying one or more layers of one or more polymers, adapted to interact with one or more of said reagents.

33. The method of claim 32, wherein one or more of said polymers is selected from a group consisting of polylysine and polyethyleneimine.

34. The method of claim 31, wherein one or more of said supports is made of at least one material selected from a group consisting of plastic, glass, nitrocellulose, nylon, polyvinylidene fluoride, and metal.

35. The method of claim 31, wherein one or more of said supports comprises one or more solid supports selected from a group consisting of rigid glass plates, rigid plastic plates, nitrocellulose membranes, nylon membranes, polyvinylidene difluoride membranes, metal membranes, and porous membranes.

36. The method of claim 22, wherein one or more of said reagents is selected from a group consisting of DNA, RNA, antibodies, peptides, proteins, enzymes, carbohydrates, oligonucleotides, recombinant vectors, drugs, viruses, bacteria, mammalian cells, small organic molecules, and large organic molecules.

37. A method for bringing two or more reagents in contact with one or more biological targets comprising the steps of,
providing an array comprising,
two or more reagents; and
one or more barriers adapted to at least temporarily maintain said reagents in at least one arrangement of two or more reagent portions so that said portions do not commingle with each other, wherein each said portion is maintained at a predefined locale in said arrangement so that each of said portions is adapted to be brought into contact with one or more predefined, biological targets;
providing one or more said biological targets on a cell growth support;
designating an address to each reagent portion based on said predefined locale and an address to each of said biological targets;
corresponding at least one of said reagent portions to at least one of said biological targets based on said designated reagent portion and biological target addresses;
contacting said predefined reagent portions with their respective corresponding biological targets;
applying one or more conditions to one or more of said reagent portions to facilitate said transfer of some or all of each specific reagent portion to said specific reagent portion's corresponding biological target, whereby some or all of each specific reagent portion dissociates from said barriers and is transferred to said specific reagent portion's corresponding biological target immobilized on said cell growth support.

38. The method of claim 37, wherein said array comprises at least two or more reagents and wherein at least one of said reagent portions comprises all or part of two or more reagents.

39. The method of claim 37, wherein one or more of said reagents is selected from a group consisting of DNA, RNA, antibodies, peptides, proteins, enzymes, carbohydrates, oligonucleotides, recombinant vectors, drugs, viruses, bacteria, mammalian cells, small organic molecules, and large organic molecules.

40. The method of claim 37, wherein one or more of said barriers comprise one or more at least partial capillary tubes.

41. The method of claim 40, wherein said barriers comprise a plurality of bundled capillary tubes.

42. The method of claim 41, wherein said barriers comprise a plurality of bundled capillary tubes.

43. The method of claim 37, wherein said barriers comprise one or more supports having at least one substantially level surface comprising a plurality of spaces surrounding and between said reagent portions wherein said reagent portions are maintained at said predefined locations so that said portions do not commingle.

44. The method of claim 43, wherein one or more of said supports comprises one or more solid supports selected from a group consisting of rigid glass plates, rigid plastic plates, nitrocellulose membranes, nylon membranes, polyvinylidene difluoride membranes, metal membranes, and porous membranes.

45. The method of claim 43, wherein one or more of said supports comprises a layer of one or more polymers adapted to immobilize one or more of said reagents.

46. The method of claim 37, wherein said step of providing one or more biological targets comprises the step of seeding and adhering two or more cells on said cell growth support.

47. The method of claim 37, wherein said step of applying one or more conditions comprises the step of applying one or more electric pulses to one or more of said reagent portions.

48. A method for bringing one or more reagents in contact with two or more biological targets comprising the steps of,
providing an array comprising,
two or more reagents; and
one or more barriers adapted to at least temporarily maintain said reagents in at least one arrangement of two or more reagent portions so that said portions do not comingle with each other, wherein each said portion is maintained at a predefined locale in said arrangement so that each of said portions is adapted to be brought into contact with one or more predefined, biological targets;
providing one or more biological targets;
designating an address to each reagent portion based on said predefined locale and an address to each of said biological targets;
corresponding at least one of said reagent portions to at least one of said biological targets based on said designated reagent portion and biological target addresses;
contacting said predefined reagent portions with their respective corresponding biological targets, whereby some or all of each specific reagent portion is transferred to said target's corresponding specific reagent portion.

49. The method of claim 37, wherein one or more of said barriers comprises one or more capillary tubes.

50. The method of claim 49, wherein said barriers compromise one or more cross-sectional slices of said capillary tubes.

51. The method of claim 37, further comprising the step of separating said cell growth support from said array.

* * * * *